United States Patent
Anapliotis et al.

(10) Patent No.: US 8,685,025 B2
(45) Date of Patent: Apr. 1, 2014

(54) CERCLAGE ARRANGEMENT FOR FIXING A BONE FRACTURE, COMPRISING A PLATE THAT IS PROVIDED WITH A NUMBER OF CONTINUOUS HOLES

(75) Inventors: Emmanuel Anapliotis, Berlin (DE); Curt Kranz, Berlin (DE)

(73) Assignee: Merete Medical GmbH, Berlin (DE)

( * ) Notice: Subject to any disclaimer, the term of this patent is extended or adjusted under 35 U.S.C. 154(b) by 1303 days.

(21) Appl. No.: 11/718,748

(22) PCT Filed: Oct. 7, 2005

(86) PCT No.: PCT/DE2005/001808
§ 371 (c)(1),
(2), (4) Date: Oct. 2, 2007

(87) PCT Pub. No.: WO2006/039900
PCT Pub. Date: Apr. 20, 2006

(65) Prior Publication Data
US 2008/0300599 A1    Dec. 4, 2008

(30) Foreign Application Priority Data
Oct. 7, 2004   (DE) ............ 20 2004 015 582 U

(51) Int. Cl.
*A61B 17/82* (2006.01)
(52) U.S. Cl.
USPC ............................................... 606/74
(58) Field of Classification Search
USPC .......................................... 606/74, 305, 329
See application file for complete search history.

(56) References Cited

U.S. PATENT DOCUMENTS

| | | | | | |
|---|---|---|---|---|---|
| 525,891 | A | * | 9/1894 | Fricke | 174/154 |
| 4,146,022 | A | * | 3/1979 | Johnson et al. | 606/74 |
| 4,790,303 | A | * | 12/1988 | Steffee | 606/300 |
| 4,887,596 | A | * | 12/1989 | Sherman | 606/305 |
| 5,067,955 | A | * | 11/1991 | Cotrel | 606/306 |
| 5,607,430 | A | | 3/1997 | Bailey | |
| 5,662,653 | A | * | 9/1997 | Songer et al. | 606/270 |
| 5,810,824 | A | * | 9/1998 | Chan | 606/70 |
| 6,110,172 | A | * | 8/2000 | Jackson | 606/305 |
| 6,520,965 | B2 | | 2/2003 | Chervitz et al. | |
| 2001/0021858 | A1 | * | 9/2001 | Bolduc et al. | 606/153 |
| 2004/0039387 | A1 | * | 2/2004 | Gause et al. | 606/69 |
| 2004/0172050 | A1 | * | 9/2004 | Bolduc et al. | 606/153 |
| 2005/0038428 | A1 | * | 2/2005 | Kelman et al. | 606/60 |

FOREIGN PATENT DOCUMENTS

WO    WO 93/03681 A1    3/1993

OTHER PUBLICATIONS

International Search Report for parent application PCT/DE2005/001808, having a mailing date of Jan. 27, 2006.

* cited by examiner

*Primary Examiner* — Christian Sevilla
(74) *Attorney, Agent, or Firm* — Andrus Intellectual Property Law, LLP

(57) ABSTRACT

A cerclage arrangement is for fixing a bone fracture and comprises a plate that is provided with at least one through-hole. A pin is equipped with a head with an opening that extends perpendicular to the direction of the pin and is used for guiding a cerclage band or wire therethrough. The cerclage pin encompasses a shaft which is provided with an end that extends through the plate so as to engage into the bone area that is to be fixed.

7 Claims, 2 Drawing Sheets

CERCLAGE ARRANGEMENT FOR FIXING A BONE FRACTURE, COMPRISING A PLATE THAT IS PROVIDED WITH A NUMBER OF CONTINUOUS HOLES

CROSS REFERENCE TO RELATED APPLICATION

The present application is the U.S. national stage application of International Application PCT/DE2005/001808, filed Oct. 7, 2005, which international application was published on Apr. 20, 2006 as International Publication WO 2006/039900. The International Application claims priority of German Patent Application 20 2004 015 582.6, filed Oct. 7, 2004.

BACKGROUND

The invention relates to a cerclage pin arrangement.

For the stabilization of a bone fraction by means of a straight or rounded trochanter plate cerclage pins are used. Round or long holes are provided in the plate, in which the cerclage pins can be inserted. In the heads of the cerclage pins throughholes are provided in crosswise arrangement, which may house cerclage bands and/or cerclage wires, forming loops around the bone area which is to be stabilized.

Such a cerclage pin arrangement is known from German utility model No. 20,214,220. With this known solution, which does not make use of bone screws, the fixation of the bone is based exclusively on the looping effect of the cerclage bands or wires.

From the U.S. Pat. No. 5,607,430 an implantable bone plate with integrated wire clamps is known, by means of which small distanced plates are provided in rail arrangement on the bone, these small plates having bores in a single direction, by means of which the cerclage wires through and around the bone are fixated. The bone rail cannot be fastened without these plates. Also no additional use of bone screws is possible. Furthermore the use is relatively time-consuming, whereby the danger exists that the small plates on the rail arrangement do not find sufficient hold for a reliable fixation.

A considerable disadvantage in all these known arrangements is that no prefixation exists, i.e. the plates rest unstably on the bone before the cerclage bands or wires are sufficiently fixed, in order to fix the plate securely. Therefore inadvertent shifts or changes of the position of the plate may occur.

From the U.S. Pat. Nos. 5,810,824 and 6,520,965 holding means for cerclage wires are known, which can be only used with bone screws. It is further known that they can take only thin cerclage wires, which effect high pressure loads on the bone. On the other hand additional bone screws are always necessary for the fixation, which for their safe fixation need an appropriate bone area according to the type of fracture. The technical solutions represented in the mentioned US-patents are thus only of limited use.

SUMMARY

An object of the invention to improve the cerclage pin specified in the documents mentioned above in such a manner that on the one hand the fixation effect is improved and on the other hand it may be used for a broad range of applications independently of the type of the fraction of the patient.

In a preferred embodiment the cerclage pin is provided with a shaft, which extends through the plate with the tapering end, in a way that it engages into the bone to be fixed, thus providing a substantial fixation of the fracture at an early stage—before the individual cerclage bands are finally tightened. According to necessity additional screws may be pivotally fixed into the round or dynamic long holes of the plate pivot, if required by the individual conditions of the fracture. They are not necessary in all cases.

If the shaft favorably is provided with a sharp or tapering into a rounded ending, it finds its way particularly easy into a prepared drilling provided by means of a normal bone drill.

If the cerclage pin in accordance with a favorable further embodiment of the invention in the head portion of the pin transverse to the direction of the pin and transverse to the direction of the opening a groove is provided, if necessary the pin can be easily driven by means of an impactor into the prepared opening.

By means of such a groove the manufacturing of the pin is eased by means of milling, since the free space available is increased for the production of the transverse openings. Also the handling to contriving the band is relieved, since this may be directly observed after the front end of the band has crossed the head portion of the pin. It is particularly favorable, if the groove in its depth is rounded and in particular ends in a semicircular shape. By this means the transition of impacting forces into the head portion is optimized, i.e. no sharp edges exist in the head area, which could cause the occurrence of tension peaks.

This will be achieved accordingly, if between head and shaft a conical or rounded range is provided, which extends from the pin to the head and in particular smoothes into the rounded range of the bone plate. By means of this it is ensured on the one hand that between head and shaft range with high loads no tension peaks occur. On the other hand there is an additional guidance with respect to the bore of the plate.

The abovementioned groove specified above may reach down into the conical or rounded range of the pin, without impairing the firmness of the head portion. The entire form of the pin being thereby optimized in such a way that the pulling effect of a relatively broad band, which produces an evenly distributed contact pressure on the bone is introduced into the pin in an optimal way and also, the adjustment stable together with the plate effectuation, by means of which local overloading of the used materials is avoided.

It is also particularly favorable that according to the invention an arrangement, consisting of pin and cerclage band, is also usable without a bone plate. This results in an extremely versatile usefulness of the arrangement according to the invention especially if it is considered that also additional bone screws may voluntarily be used according to requirements.

In another favorable embodiment pins are packed individually in each case with a cerclage band (sterile), so that the physician according to the necessities of the individual application—always have the necessary number of pins and bands at hand.

In a preferred embodiment the cerclage pin according to the invention consists of a body-compatible implant material, in particular an alloy such as CrNi or CrMo.

The cerclage pin according to the invention exhibiting a sharp or rounded tip that extends through an opening of the bone plate, is brought into a prepared drilling prepared within the bone range and placed together with the stabilization plate on and/or over the region of the fracture thereby ensuring is a safe prefixation. Subsequently, the cerclage band or wire is pushed and fastened by means of the openings of the cerclage pins, so that the fracture is stably fastened on both of its ends.

Thus the use of cerclage pins with a fixing point permits an eased mounting of a stabilizing or trochanter plate in the technique of the cerclage band fixation. It may however be also used individually—either in a supplementing or separate way.

BRIEF DESCRIPTION OF THE DRAWINGS

Further favorable embodiments may be seen from the following description of preferred embodiments and on the basis of the respective designs wherein.

DETAILED DESCRIPTION OF THE DRAWING

Figure 1:
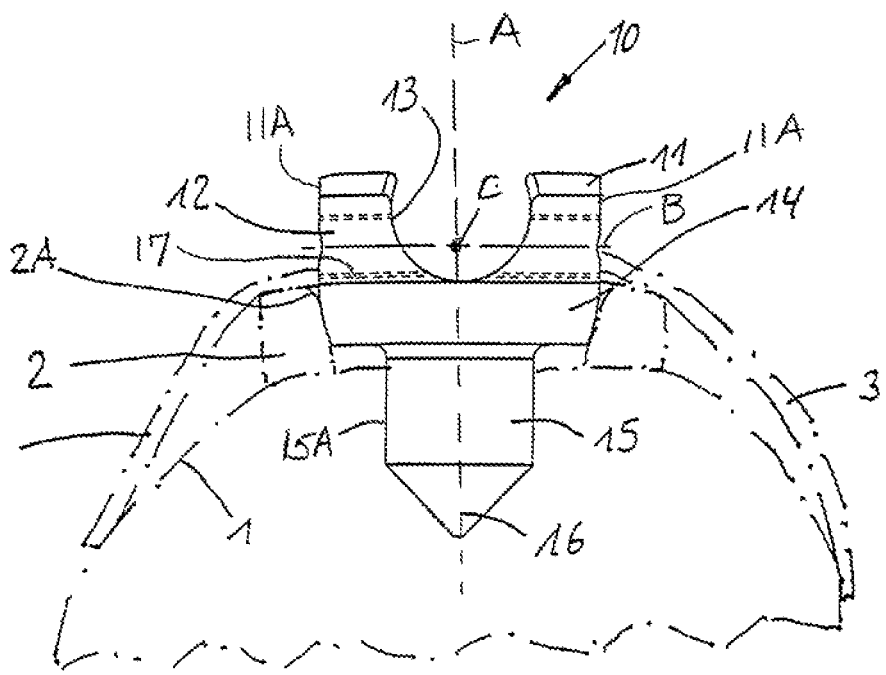
FIG. 1 is a view of the cerclage arrangement according to invention.

In FIG. 1 the cerclage pin arrangement according to invention is shown. The fracture area—in dash-dotted representation—of bone 1 is fixed by means of a stabilization plate 2, a cerclage band 3 (likewise—in dash-dotted representation) and a cerclage pin 10.

The cerclage pin 10 extends along a vertical central axis A and is provided with a partially cylindrical head 11 having a transverse opening 12 extending along a horizontal axis B and a groove 13 of semicircular form extending along a horizontal axis C and defining an impact surface, into which an impactor, thus forming the impact tool, is applicable. The head 11 has truncated flat, spaced apart outer sidewalls 11A through which the opening 12 passes along an entire length l of the outer sidewalls 11A. Underneath the head 11 a cone section 14 is provided, which fits into the lower region of the at least one throughhole 2A of the stabilization plate 2. The groove 13 extends continuously from a top surface of the come section 14, and down into a flat bottom wall 17 of the head 11 that guides the band 3 through the opening 12. Adjacent to the head portion a cylindrical shaft 15 having a smooth unthreaded external surface 15A throughout its length with a smooth tip or end 16 is provided.

Figure 2:
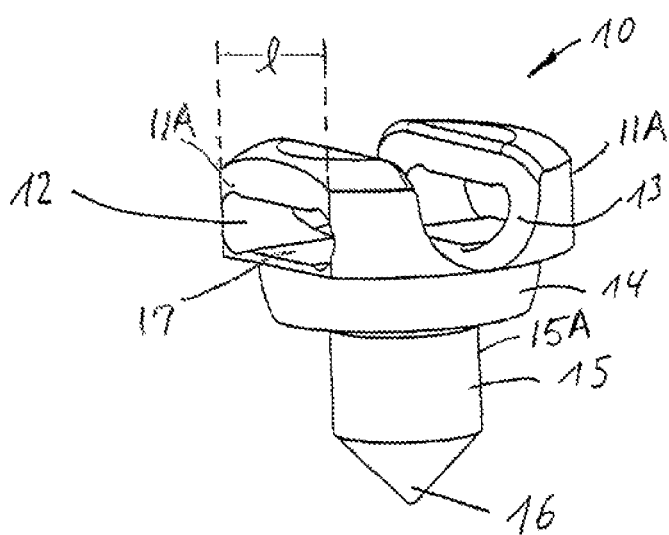
FIG. 2 shows a cerclage pin in perspective view as part of the arrangement represented in FIG. 1.
Figure 2A:
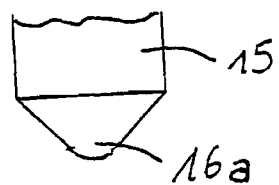
FIG. 2a shows a first further embodiment of the cerclage pin arrangement represented in FIG. 2 as well as FIG. 2b shows a second further embodiment of the cerclage pin arrangement represented in FIG. 2.
Figure 2B:

For the fixation of a bone fracture zone the cerclage pin 10 is provided with a plate 2 exhibiting the at least one throughhole 2A and preferably a number of throughholes, whereby to would drive through in the head of the pin provided and the opening 12 exhibiting transverse to the direction of the pin a cerclage bands or wire serves. By the groove 13, the opening 12 is divided into two ranges, so that introducing the band 3 to the opening 12 may easily be observed. In the range of the head 11 provided, the axis C of the groove 13 is arranged transverse to the axis A of the pin 10 and also transverse to the axis B of the opening 12. The groove 13 is in its depth semicircular rounded. Furthermore the cerclage pin 10 is provided in the range of its shaft at its end 16 with a point or tapering into a rounded or blunt ending. The two embodiments are in the FIGS. 2a and 2b—as partial representations of FIG. 2 shown, whereby the shaft 15 alternatively may be provided with a rounded point 16a (FIG. 2a) or a blunt end of 16b (FIG. 2b). The selection of the individual forming of the tip has to be decided according to desired application. Whereby the firmness of the pin rises with increasing blunting on the one hand while on the other hand an increased taper of the end facilitates the introducing of the pin into a drilling bore. For a broad applicability, an intermediate solution will be selected here, as it corresponds for example to the example shown in FIG. 2b.

Between head portion 11 and the shaft 15, a conical or rounded range 14 is provided, which extends from the pin to the head and fits in particular into the roundness range against a rounded or slotted wall forming the hole 2A of the plate 2.

Using, as first the stabilization plate 2 is brought on and/or over the fraction type, by the holes 12 bag drilling with defined depth and smaller diameter than the shaft 15 is taking place, is brought and then the cerclage pin 10 is easily driven into the bone by means of an impactor.

The cerclage pin 10 preferably consists of a stainless metal alloy for surgical purposes for example CrNi or CrMo or another metal alloy suitable for the implantation manufactured.

As it is not represented here in detail—the cerclage band is formed by a flexible metal band, which likewise consists of an implantable material. After this has been pulled through the head portion of the pin and lead around the bone being connected as a loop, its appropriate connecting devices end are provided. These consist preferentially of an eye into those the end of the band are introduced and then bent sharply and led back.

Packing units are formed by in each case one with a cerclage band together sterile packed pin, so that on the one hand for each application easily the necessary parts can be arranged—on the other hand however a different provision with stocks also to many embodiments is avoided.

The invention is not limited by the represented example, but also other combinations may be favorably used.

The invention claimed is:

1. A cerclage arrangement used in fixing a bone fracture in a bone area, the cerclage arrangement comprising:
a cerclage pin extending along a vertical axis and including a head, a shaft depending beneath the head and a cone or rounded section positioned between the head and the shaft, the head being formed with an opening that extends along a first horizontal axis which is perpendicular to the vertical axis, the head having spaced apart outer sidewalls through which the opening passes, the head being constructed with a flat, bottom wall that extends through the opening, and a rounded groove that extends continuously from a top surface of the head into the flat bottom wall, the groove extending along a second horizontal axis that is perpendicular to the vertical axis and the first horizontal axis, the shaft having a smooth unthreaded external surface which terminates in a smooth end having a pointed or blunt tip;
a plate formed with wall structure defining at least one throughhole for receiving and retaining the cone or rounded section of the cerclage pin; and
a flexible band or wire engaged by the head and the plate and received through the opening,
whereby the cerclage pin together with the plate is capable of being positioned over the bone fracture in the bone area to be fixed, and an impacting force is capable of being applied to the groove to fix the shaft and the end in the bone area after which, the flexible band or wire is capable of being passed through the opening, and capable of being engaged along the flat bottom wall and the plate, and capable of being secured to a bone containing the bone fracture, the flexible band or wire being configured to provide a pulling effect which is capable of producing an evenly distributed contact pressure on the bone.

2. The cerclage pin of claim 1, wherein the opening passes along an entire length of the outer sidewalls.

3. The cerclage pin of claim 1, wherein the groove defines an impact surface adapted to be impacted by an impactor for driving the shaft and the end into the bone area.

4. The cerclage pin of claim 1, wherein the head is partially cylindrical.

5. The cerclage pin of claim 1, wherein the head, the shaft and the cone or rounded section are constructed of a body-compliant implant material.

6. The cerclage arrangement of claim 1, wherein the at least one throughhole in the wall structure is adapted to overlie the bone area to be fixed, the cone or rounded section being engaged against the wall structure and the shaft passing through the throughhole.

7. The cerclage arrangement of claim 1, wherein the cerclage pin and the flexible band are constructed of a body-compliant implant material.

* * * * *